(12) United States Patent
Golz-Berner et al.

(10) Patent No.: US 6,221,372 B1
(45) Date of Patent: Apr. 24, 2001

(54) COSMETIC CLEANSING AND SKIN CARE PREPARATION CONTAINING PLANT AND ALGAE EXTRACTS

(75) Inventors: Karin Golz-Berner; Leonhard Zastrow, both of Monaco (MC)

(73) Assignee: Lancaster Group GmbH, Mainz (DE)

( * ) Notice: Subject to any disclaimer, the term of this patent is extended or adjusted under 35 U.S.C. 154(b) by 0 days.

(21) Appl. No.: 09/319,090

(22) PCT Filed: Dec. 12, 1997

(86) PCT No.: PCT/DE97/02935

§ 371 Date: May 28, 1999

§ 102(e) Date: May 28, 1999

(87) PCT Pub. No.: WO98/26755

PCT Pub. Date: Jun. 25, 1998

(30) Foreign Application Priority Data

Dec. 18, 1996 (DE) ................................. 196 54 508

(51) Int. Cl.⁷ ............................. A61K 7/48; A61K 9/107
(52) U.S. Cl. .................. 424/401; 424/195.1; 424/78.02; 424/724; 514/937
(58) Field of Search ................. 424/195.1, 401, 424/78.02, 724; 514/937

(56) References Cited

FOREIGN PATENT DOCUMENTS

| | | |
|---|---|---|
| 0 565 495 | 4/1993 | (EP) . |
| 0 721 755 | 7/1996 | (EP) . |
| 0 728 474 | 8/1996 | (EP) . |
| 2715070 | 7/1995 | (FR) . |
| 61-286317 | 12/1986 | (JP) . |
| 63-057510 | 3/1988 | (JP) . |
| 6-256140 | 9/1994 | (JP) . |
| 2006223 | 1/1994 | (RO) . |
| 96/17588 | 6/1996 | (WO) . |

OTHER PUBLICATIONS

N. Mekideche et al "Die Geheimnisse des Meeres", Parfumerie und Kosmetik, 76, No. 12/95, pp. 776 to 779.

Dweck, "Treasure Chest of the Deep", Soap, Perfumery & Cosmetics 64, Jun. 1991, No. 6, pp. 40 to 43.

*Primary Examiner*—Raj Bawa
(74) *Attorney, Agent, or Firm*—Collard & Roe, P.C.

(57) ABSTRACT

The invention relates to a cosmetic cleansing and skin care preparation which is particularly suitable for extremely greasy pubertal skin and exhibits very good sebostatic effectiveness. The preparation contains 0.25–5 wt. % of a combination comprising 5–40 wt. % of an alga laminaria saccharina extract; 10–60 wt. % of lilium candidum root extract; 10–50 wt. % glycyrrehetinic acid as a natural extract of glycyrrhiza glabra. The preparation also contains 99.75 to 95 wt. % cosmetic auxiliary agents and carriers, optionally mixed with additional active substances.

7 Claims, No Drawings

COSMETIC CLEANSING AND SKIN CARE PREPARATION CONTAINING PLANT AND ALGAE EXTRACTS

BACKGROUND OF THE INVENTION

1. Field of the Invention

This invention concerns a cosmetic cleansing and skin care preparation which is suitable in particular for oily skin, which often also has inflamed spots or areas, such as skin during puberty or skin exposed to particular environmental toxins.

2. The Prior Art

A number of cosmetic preparations that have already been proposed or have come on the market are especially suitable for problem skin with excess oil and sebum secretion as well as inflamed spots or areas. European Patent No. 721,775 A describes a combination of (a) salicylic acid and/or an α-hydroxycarboxylic acid and/or an α-ketocarboxylic acid, (b) a glycerine monocarboxylate monoester and (c) optionally retinol or a retinol derivative. European Patent No. 728,474 A describes the use of a compound having at least one incompletely neutrlized sulfonic acid function as an anti-acne agent in the preparation of topical formulations.

It is known from the journal Parfümerie und Kosmetik [Perfumery and Cosmetics], No. 12, 1997, pages 776–779 that phlorogine as a basic ingredient in a marine alga combats excess sebum in skin and hair.

Japanese Patent No. 61-286,317-A, which is abstracted in Patent Abstracts of Japan 1987, volume 11, no. 150, describes the use of an aqueous extract of Glycyrriza glabra in bath preparations.

Japanese Patent No. 6-256,140 A, which is abstracted in Patent Abstracts of Japan 1994, volume 18, no. 651, describes a combination of glycyrrhetic acid derivatives and a water-soluble UV absorbent as a skin care preparation.

The effects that can be achieved with proposed formulations and preparations already available on the market are not always satisfactory, however.

SUMMARY OF THE INVENTION

The object of this invention is to provide new cosmetic cleansing and skin care preparations that are especially suitable for oily and inflamed skin, especially skin during puberty, and have a high efficacy.

According to this invention, a cosmetic cleansing and skin care preparation containing 0.25 to 5 wt % of a combination consisting of the following ingredients is made available:

5 to 40 wt % of an extract of *Laminaria saccharina* alga; 10 to 60 wt % of a root extract of *Lilium candidum;* 10 to 50 wt % glycyrrhetic acid as a natural root extract of *Glycyrriza glabra;* and the preparation also contains 99.75 to 95 wt % cosmetic additives and vehicles, optionally in mixture with other active ingredients.

It is known from research that an extract of *Laminaria saccharina,* for example, inhibits the lipase enzyme, a hydrolase which specifically cleaves triglycerides into glycerine and fatty acids, thereby preventing the formation of free fatty acids as well as prostaglandins. However, adding less than 0.8% of the extract yields less than 20% inhibition of lipase and therefore cannot be regarded as very effective. Therefore adding at least 1% of this extract has been proposed for effective inhibition of approximately 30% lipase.

It has surprisingly been found that a combination of the above ingredients with a *Laminaria saccharina* content significantly less than 0.8 wt % achieves a sebostatic effect of approximately 30% or more, so this is an unforeseeable increase in effect (synergism). With the addition of 2% of the alga based on the total weight the preparation, approximately 80% lipase inhibition is achieved. This can be ascertained by fatty acid assays.

Nor could it have been foreseen that the new preparation would not affect the endogenous microflora of healthy skin or that the full activity of the two other ingredients of the combination would be maintained completely.

The root extract of *Lilium candidum* normally has a tonic and astringent effect, and in the present case it also contributes toward an increase in the sebostatic effect.

Glycyrrhetic acid is known to promote wound healing and is effective against itchy skin, and previously it has also been used for allergic reactions, rough or chapped skin in face lotions and creams. In the present case it surprisingly also contributes toward increasing the sebostatic effect.

As another active ingredient, the preparation may also advantageously (according to International Patent WO 96/17588) contain kaolin modified with spherical $Tio_2$ or $Sio_2$ particles with a particle size of <5 μm, where the spherical particles amount to 0.5 to 10 wt % of the kaolin mixture. The preparation thus has a very soft feel on skin while also having an anti-inflammatory effect.

The modified kaolin may be present in the amount of 0.1 to 6 wt %, based on the total amount of preparation.

The preparation may also contain as another active ingredient a Matricaria recutita floral extract in the amount of 0.1 to 1 wt %, based on the total weight of the preparation. This plant extract is present in many cosmetic and dermatological preparations and has an anti-inflammatory effect on the skin, especially due to its bisabolol content.

This new preparation is especially suitable for oily and inflamed skin, especially adolescent skin, and is highly effective on such problem skin areas. Secretion of oil is greatly reduced while at the same time inflammations are eliminated within a short period of time or are at least suppressed perceptibly. It is also possible to further increase the concentration of the three ingredients of the combination that are essential to this invention, leading to a further improvement in effect, although this is not as pronounced as that achieved with the present concentrations.

The preparation according to this invention also contains cosmetic additives and vehicles such as those generally used in such preparations, e.g., water, preservatives, vitamins, coloring agents, pigments with a coloring effect, radical scavengers, thickeners, softeners, moisturizing substances, perfumes, alcohols, polyols, polymers, copolymers, emulsifiers.

The pH of the preparation may be adjusted to advantage in the acidic range, with a preferred pH being from 5 to 6.

It is prepared by first preparing the complex by stirring together 5 to 40 wt % alga, 10 to 60 wt % root extract and 10 to 50 wt % glycyrrhetic acid at 15 to 35° C. In addition, suitable amounts of modified kaolin (according to International Patent WO96/17588) and camomile extract may also be added while stirring to further increase the effect.

It is also possible to make this preparation in a two-phase form, for example, as a two-phase tonic agent by mixing the phases together at room temperature while stirring.

DETAILED DESCRIPTION OF THE DESCRIPTIONS

The present invention will be explained in greater detail below on the basis of examples. All amounts are given in wt %. The amount of water which is added to yield 100% is based on 100% of the total formulation.

EXAMPLE 1

Face Mask

| Phase A | |
|---|---|
| Copolymer | 1.5 |
| Carbomer | 0.5 |
| Propylene glycol | 1.0 |
| Glycerine | 1.5 |
| Kaolin, normal | 25.0 |
| Kaolin, modified | 5.0 |
| Water | to a total of 100 |
| Phase B | |
| Jojoba oil | 2.0 |
| Babassu oil | 2.0 |
| Cetearyl alcohol | 2.5 |
| Phase C | |
| TEA (triethanolamine) | 0.8 |
| Phase D | |
| Preservative | 0.4 |
| Perfume | 0.5 |
| Phase E | |
| Laminaria saccharina extract | 40 |
| Lilium candidum extract | 45 |
| Glycyrrhetic acid | 10 |
| Matricaria recutita extract | 5 |

Phases A and B were heated separately to about 60 to 65° C. and mixed together while stirring. Then phase C was added and the mixture was cooled to 40° C. Next, phase D was stirred in. Then 2.5 wt % of phase E, based on the total weight of the preparation, was stirred with the mixture of the other phases, and cooled to a maximum of 35° C., yielding a homogeneous mixture.

EXAMPLE 2

Cream

| Phase A | |
|---|---|
| Carbomer | 0.8 |
| Propylene glycol | 2.5 |
| Glycerine | 2.5 |
| Water | to a total of 100 |
| Phase B | |
| Jojoba oil | 2.5 |
| Calendula oil | 1.5 |
| Palm oil | 1.5 |
| Cetearyl alcohol | 1.5 |
| Phase C | |
| TEA (triethanolamine) | 0.5 |
| Phase D | |
| Aloe vera | 2 |
| Quince extract | 1 |
| Phase E | |
| Laminaria saccharina extract | 34 |
| Lilium candidum extract | 25 |

| -continued | |
|---|---|
| Glycyrrhetic acid | 25 |
| Matricaria recutita extract | 16 |

The ingredients were mixed as described in Example 1, also adding 1.5% modified kaolin, and phase E amounted to 5% of the total composition.

EXAMPLE 3

Two-Phase Tonic Preparation

| Phase A | |
|---|---|
| Ethanol | 7 |
| Propylene glycol | 1 |
| Glycerine | 2 |
| Preservative | 0.4 |
| Modified kaolin | 10.0 |
| Water | to a total of 100 |
| Phase B | |
| Laminaria saccharina extract | 20 |
| Lilium candidum extract | 50 |
| Glycyrrhetic acid | 25 |
| Matricaria recutita extract | 5 |

Phases A and B were mixed together at room temperature, with the amount of phase B in the total composition being 1.0%.

EXAMPLE 4

Cleansing Gel

| Phase A | |
|---|---|
| Carbomer | 1.5 |
| Propylene glycol | 1.0 |
| Glycerine | 1.0 |
| Water | to a total of 100 |
| Phase B | |
| TEA (triethanolamine) | 1.5 |
| Phase C | |
| Ginseng extract | 1.0 |
| Perfume | 0.2 |
| Preservative | 0.3 |
| Tegobetaine | 1.5 |
| Phase D | |
| Laminaria saccharina extract | 35 |
| Lilium candidum extract | 22 |
| Glycyrrhetic acid | 33 |
| Matricaria recutita extract | 10 |

The ingredients were mixed as in Example 1, with the amount of phase D in the total composition being 3.8%.

What is claimed is:

1. A cosmetic cleansing and skin care preparation comprising
   (a) 0.25 to 5 wt % of an active ingredient combination of 5 to 40 wt % of an extract of *Laminaria saccharina*

*alga;* 10 to 60 wt % of a root extract of *Lilium candidum;* 10 to 50 wt % glycyrrhetic acid as a natural extract *Glycyrriza glabra;* and (b) 99.75 to 95 wt % cosmetic additives and vehicles.

2. A preparation according to claim 1, further comprising an additional active ingredient selected from the group consisting of kaolin, floral extract, and plant extract.

3. A preparation according to claim 2, wherein the additional active ingredient comprises a kaolin mixture of kaolin modified with spherical particles selected from the group consisting of $TiO_2$ and $SiO_2$ with a particle size of <5 μm, with the spherical particles being present in the amount of 0.5 to 10 wt % of the kaolin mixture.

4. A preparation according to claim 3, wherein the kaolin mixture amounts to 0.1 to 1 wt %, based on the total weight of the preparation.

5. A preparation according to claim 2, wherein the additional active ingredient comprises a floral extract of *Matricaria recutita,* the amount being 0.1 to 1 wt %, based on the total weight the preparation.

6. A preparation according to claim 1, wherein the active ingredient combination of (a) comprises 0.5 to 4 wt %.

7. A preparation according to claim 1, wherein the extract of the *Laminaria saccharina* alga in the active ingredient combination comprises 5 to 20 wt %.

\* \* \* \* \*